(12) United States Patent
Kunzendorf et al.

(10) Patent No.: US 10,301,375 B2
(45) Date of Patent: May 28, 2019

(54) TAT-CRMA ANTI-APOPTOTIC FUSION PROTEINS

(71) Applicant: Unipeak Consulting SDN BHD, Kuala Lumpur (MY)

(72) Inventors: Ulrich Kunzendorf, Kiel (DE); Stefan Krautwald, Flintbek (DE)

(73) Assignee: Unipeak Consulting SDN BHD, Kuala Lumpur (MY)

( * ) Notice: Subject to any disclaimer, the term of this patent is extended or adjusted under 35 U.S.C. 154(b) by 0 days.

(21) Appl. No.: 15/205,838

(22) Filed: Jul. 8, 2016

(65) Prior Publication Data

US 2017/0152302 A1 Jun. 1, 2017

Related U.S. Application Data

(62) Division of application No. 13/128,085, filed as application No. PCT/EP2009/064937 on Nov. 10, 2009, now Pat. No. 9,388,219.

(30) Foreign Application Priority Data

Nov. 10, 2008 (EP) .................................... 08168730

(51) Int. Cl.
 *C07K 14/81* (2006.01)
 *C07K 7/06* (2006.01)
 (Continued)

(52) U.S. Cl.
 CPC ........ *C07K 14/8121* (2013.01); *C07K 14/005* (2013.01); *C07K 14/811* (2013.01);
 (Continued)

(58) Field of Classification Search
 None
 See application file for complete search history.

(56) References Cited

U.S. PATENT DOCUMENTS 6,046,007 A 4/2000 Dixit
6,472,176 B2 10/2002 Kovesdi et al.
 (Continued)

OTHER PUBLICATIONS

Nagahara et al., Transduction of full-length TAT fusion proteins into mammalian cells: TAT-p27kip1 induces cell migration, Nat. Med. 4(12):1449-1452, Dec. 1998.*
 (Continued)

*Primary Examiner* — Claire Kaufman
(74) *Attorney, Agent, or Firm* — Schwegman Lundberg & Woessner, P.A.

(57) ABSTRACT

The present invention relates to a fusion protein comprising a protein transduction domain capable of introducing the fusion protein into a mammalian cell and an anti-apoptotic protein comprising the amino acid of the sequence of SEQ ID NO:1 or an anti-apoptotically active variant or fragment thereof. The invention also relates to a pharmaceutical composition comprising such a fusion protein, in particular for blocking apoptosis in a patient in need thereof. The invention also provides a polynucleotide encoding such a fusion protein, an expression vector comprising the polynucleotide and a host cell comprising the expression vector. In a further aspect, the invention relates to the use of any of theses materials for the preparation of a medicament for blocking apoptosis in a patient in need thereof.

10 Claims, 4 Drawing Sheets

Specification includes a Sequence Listing.

(51) Int. Cl.
    *C07K 14/005*     (2006.01)
    *A61K 38/00*     (2006.01)

(52) U.S. Cl.
    CPC .......... *A61K 38/00* (2013.01); *C07K 2319/10* (2013.01); *C12N 2710/24122* (2013.01)

(56) References Cited

U.S. PATENT DOCUMENTS

| | | |
|---|---|---|
| 9,388,219 B2 | 7/2016 | Kunzendorf et al. |
| 2002/0110869 A1 | 8/2002 | Kovesdi et al. |
| 2004/0219147 A1 | 11/2004 | Bell |
| 2006/0263382 A1 | 11/2006 | Hotchkiss et al. |
| 2011/0318318 A1 | 12/2011 | Kunzendorf et al. |

OTHER PUBLICATIONS

GenBank Database Accession No. O72749/UniProtKB locus O72749_C0WPX, B12R protein, [Online] retrieved from the internet: <http://www.ncbi.nlm.nih.gov/protein/o72749>, accessed Aug. 22, 2013, (Aug. 1, 1998).
Chinese Application No. 200980146384.5, First Office Action dated Jul. 15, 2013, with English translation, [for nationalized application of prior application PCT/EP2009/064937], 14 pgs.
Chinese Application No. 200980146384.5, Second Office Action dated Feb. 28, 2014, [for nationalized application of prior application PCT/EP2009/064937], 9 pgs.
Chinese Application No. 200980146384.5, Third Office Action dated Nov. 25, 2014, [for nationalized application of prior application PCT/EP2009/064937], 8 pgs.
Japanese Application No. 2011-535138, Office Action, [for nationalized application of prior application PCT/EP2009/064937], 5 pgs.
U.S. Appl. No. 13/128,085, Final Office Action dated Aug. 29, 2013, 12 pgs.
U.S. Appl. No. 13/128,085, Non Final Office Action dated Apr. 1, 2015, 10 pgs.
U.S. Appl. No. 13/128,085, Non Final Office Action dated Dec. 4, 2012, 14 pgs.
U.S. Appl. No. 13/128,085, Notice of Allowance dated Mar. 15, 2016, 8 pgs.
U.S. Appl. No. 13/128,085, Notice of Allowance dated Oct. 5, 2015, 11 pgs.
U.S. Appl. No. 13/128,085, Response filed Feb. 28, 2014 to Final Office Action dated Aug. 29, 2013, 7 pgs.
U.S. Appl. No. 13/128,085, Response filed Jun. 4, 2013 to Non-Final Office Action dated Dec. 4, 2012, 10 pgs.
U.S. Appl. No. 13/128,085, Response filed Jul. 31, 2015 to Non Final Office Action dated Apr. 1, 2015, 7 pgs.
U.S. Appl. No. 13/128,085, Response Filed Sep. 26, 2012 to Restriction Requirement dated Aug. 30, 2012, 6 pgs.
U.S. Appl. No. 13/128,085, Restriction Requirement dated Aug. 30, 2012, 7 pgs.
European Application Serial No. EP08168730, European Search Report dated Mar. 17, 2009, 2 pgs.
International Application Serial No. PCT/EP2009/064937, International Search Report dated Dec. 17, 2009, 2 pgs.
International Application Serial No. PCT/EP2009/064937, Written Opinion dated Dec. 17, 2009, 5 pgs.
Becker-Hapak, M., et al., "TAT-Mediated Protein Transduction into Mammalian Cells", Methods, 24, (2001), 247-256.
Bhorade, R., et al., "Macrocyclic Chelators with Paramagnetic Cations Are Internalized into Mammalian Cells via a HIV-Tat Derived Membrane Translocation Peptide", Bioconjugate Chemistry, 11(3), (2000), 301-305.
Dietz, G. P. H., et al., "Inhibition of Neuronal Apoptosis in Vitro and in Vivo Using TAT-Mediated Protein Transduction", Molecular and Cellular Neuroscience, 21, (2002), 29-37.

Dobo, et al., "Cytokine response modifier A inhibition of initiator caspases results in covalent complex formation of dissociation of caspase tetramer", J. Biol. Chem. 281 (50), (Dec. 2006), 38781-38790.
Ekert, et al., "Inhibition of apoptosis and clonogenic survival of cells expressing crmA variants: optimal caspase substrates are not necessaril optimal inhibitors", EMBO J., 18(2), (1999), 330-338.
Green, M., et al., "Autonomous Functional Domains of Chemically Synthesized Human Immunodeficiency Virus Tat Trans-Activator Protein", Cell, 55, (1988), 1179-1188.
Gross, Atan, et al., "BCL-2 Family Members and the Mitochondria in Apoptosis", Genes and Development, 13, (1999), 1899-1911.
Huang, et al., "In vivo myocardial infarct size reduction by a caspase inhibitor administered after the onset of ischemiia", Eur. J.Pharm. 402, (2000), 139-142.
Ju, et al., "Anti-apoptotic therapy with a Tat fusion protein protects against excitotoxic insults in vitro and in vivo", Exp. Neuobiol. 210, (2008), 602-607.
Kempf, T., et al., "The Transforming Growth Factor-B Superfamily Member Growth-Differentiation Factor-15 Protects the Heart From Ischemia/Reperfusion Injury", Circulation Research, 98, (2006), 351-360.
Krautwald, S., et al., "Transduction of the TAT-FLIP Fusion Protein Results in Transient Resistance to Fas-induced Apoptosis in Vivo", The Journal of Biological Chemistry, 279(42), (2004), 44005-44011.
Li, et al., "Critical roles for the fas/fas ligand system in postinfarction ventricular remodeling and heart failure", Circ. Res. 95 :627-636, (2004).
Li, et al., "CrmA gene can protect hepatocyte apotosis induced by anti-Fas antibody in mice", Transplantation, 67(7):S114, Abst. #431, (Apr. 15, 1999).
Mocanu, et al., "Caspase inhibition and Limitation of myocardialin farct size: protection against lethal reperfusion injury", Br. J.Pharm .130, (2000), 197-200.
Rami, et al., "Exploiting endogenous anti-apoptotic proteins for novel thereapeutic strategies in cerebral ischemia", Prog. Neurobiol. 85, (Jul. 2008), 273-296.
Simonovic, et al., "Lack of involvment of strand s1'A of the viral serpin crmA in anti-apoptotic or caspase-inhibitory functions", Arch. Biochem. Biophys. 44, (2005), 1-9.
Siu, et al., "Doxorubic ininduces caspase-independent apoptosis in transgenic mice overexpressing CrmA", Circ. 114:11 532, (2006).
Tewari, M., et al., "CrmA, a Poxvirus-encoded Serpin, Inhibits Cytotoxic T-lymphocyte-mediated Apoptosis", The Journal of Biological Chemistry, 270(39), (1995), 22705-22708.
Tewari, M., et al., "Fas- and Tumor Necrosis Factor-induced Apoptosis is Inhibited by the Poxvirus crmA Gene Product", The Journal of Biological Chemistry, 270(7), (Feb. 17, 1995), 3255-3260.
Voortman, et al., "TRAIL therapy in non-small cell lung cancer cells: sensitization to death receptor-meidated apoptosis by proteasorne inhibitor bortezomib", Mol. Cancer Ther. 6, (2007), 2103-2112.
Wender, P. A., et al., "The design, synthesis, and evaluation of molecules that enable or enhance cellular uptake: Peptoid molecular transporters", Proc. Natl. Acad. Sci. USA, 97(24), (2000), 13003-13008.
Park, J., et al., "Mutational analysis of a human immunodeficiency virus type 1 Tat protein transduction domain which is required for delivery of an exogenous protein into mammalian cells", Journal of General Virology, 83, (2002), 1173-1181.
"Excerpt: Human c-FLIPS", from "CASP8 and FADD-like apoptosis regulator—Gene: CFLAR", Uniprot.org, 2018. Retrieved on Oct. 15, 2018. Retrieved from the Internet: < https://www.uniprot.org/uniprot/O15519#O15519-1 >, 14 pgs.
"Excerpt: Murine Bcl-X", from "CASP8 and FADD-like apoptosis regulator—Gene: CFLAR", Uniprot.org, 2018. Retrieved on Oct. 15, 2018. Retrieved from the Internet: < https://www.uniprot.org/uniprot/O15519#O15519-1 >, 14 pgs.

* cited by examiner

TAT-CRMA ANTI-APOPTOTIC FUSION PROTEINS

CLAIM OF PRIORITY

This application is a divisional of and claims the benefit of priority under 35 U.S.C. § 120 to U.S. patent application Ser. No. 13/128,085, filed on Aug. 18, 2011, which is a U.S. National Stage Filing under 35 U.S.C. 371 from International Application No. PCT/EP2009/064937, filed on Nov. 10, 2009, and published as WO 2010/052341 A1 on May 14, 2010, which claims priority to European Patent Application No. 08168730.3, filed Nov. 10, 2008; which applications and publication are incorporated herein by reference in their entirety.

The present invention relates to a fusion protein comprising a protein transduction domain capable of introducing the fusion protein into a mammalian cell and an anti-apoptotic protein comprising the amino acid of the sequence of SEG ID NO:1 or an anti-apoptotically active variant or fragment thereof. The invention also relates to a pharmaceutical composition comprising such a fusion protein, in particular for blocking apoptosis in a patient in need thereof. The invention also provides a polynucleotide encoding such a fusion protein, an expression vector comprising the polynucleotide and a host cell comprising the expression vector. In a further aspect, the invention relates to the use of any of theses materials for the preparation of a medicament for blocking apoptosis in a patient in need thereof.

BACKGROUND OF THE INVENTION

The regulation of the cell number in multicellular organisms is an essential requirement both for the development of the organism and the maintenance of its different vital functions. Apoptosis is a process in which cells that are not required at a certain stage of development undergo a programmed cell death. For example, it is the precisely regulated interplay of proliferation and apoptosis that is responsible for shaping tissues and organs in the developing embryo. Apoptosis is induced by a number of different stimuli and propagated by different pathways.

The extrinsic pathway inter alia includes binding of the death receptor ligands, e.g. TNF, TRAIL and CD95L, to their respective receptor molecules in the cell, which binding ultimately activates caspase-8. The intrinsic pathway is stimulated, for example, through application of the DNA-damaging topoisomerase inhibitors doxorubicin, etoposide and staurosporine, TCR stimulation, irradiation, DNA damage and the like, which results in the release of cytochrom c from mitochondria, activation of caspase-9, and the granzyme B-dependent route to caspase activation. Granzyme B can process BID as well as caspase-3 and -7 to initiate apoptosis. These pathways are linked so that they affect each other. Cells which undergo apoptosis regularly show a number of characterizing features, such as chromatin condensation, cell shrinkage, increased membrane permeability and internucleosomal DNA cleavage.

Apart from its different functions during development, an impaired, increased or defective apoptosis is also involved in a number of diseases or pathological conditions. For example, ischemia and subsequent reperfusion induces apoptosis both via the intrinsic and extrinsic pathway which can lead to a complete failure o crucial tissues or organs the function of which are essential for the organism. For example, an abnormally increased extent of apoptosis may result in renal failure and brain tissue damage. Further, it has been reported that an increased apoptosis is also involved in gastrointestinal disorders. In contrast, an abnormally decreased apoptosis is involved in different forms of cancer.

Although different inhibitors of apoptosis have been suggested in the prior art, none of these approaches has proven suitable for clinical practice. For example, different anti-apoptotic proteins have been discussed as therapeutic compounds. However, the clinical use of these proteins is presently only possible using gene transfer methods which involve unforeseeable risks for the patients undergoing such treatment. Therefore, it is an objective of the present invention to provide means and methods for a save and efficient treatment of an abnormally increased apoptosis. This objective is achieved by a fusion protein comprising a protein transduction domain capable of introducing the fusion protein into a mammalian cell and an anti-apoptotic protein as further defined herein.

Figure 1:
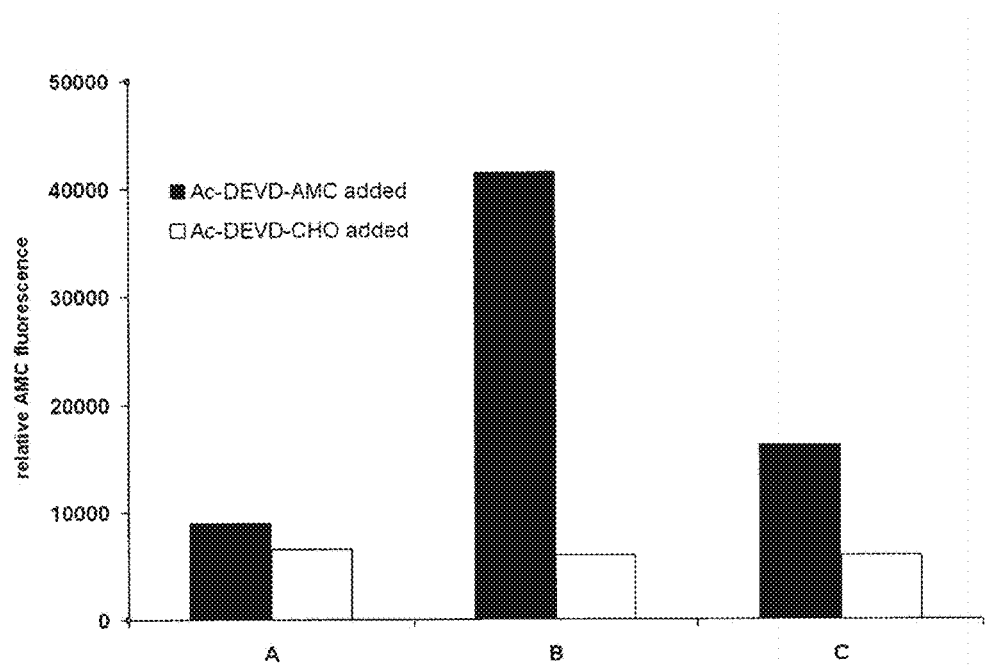
FIG. 1 shows the results from in vitro assays demonstrating that TAT-CrmA is capable of blocking activity of caspase-3, an early marker of cells undergoing apoptosis. Lysates used were derived from untreated Jurkat cells (A), Jurkat cells treated with anti-Fas antibody (B) or Jurkat cells treated with TAT-CrmA prior to the addition of anti-Fas antibody (C).

According to the present invention, it has now been surprisingly found that the coupling of the cowpox virus cytokine response modifier A (CrmA) protein to a protein transduction domain, such as the protein transduction domain of the HIV Tat protein, results in an anti-apoptotically active fusion protein which is effective in blocking apoptosis in a patient in need of an anti-apoptotic treatment, i.e. a patient suffering from a disease characterized by a pathogenic level of apoptosis in cells or tissues of the body.

Accordingly, a fusion protein is provided, said fusion protein comprising at least the following components:
(a) a protein transduction domain capable of introducing the fusion protein into a mammalian cell;
(b) an anti-apoptotic protein comprising the amino acid sequence of SEQ ID NO:1 or an anti-apoptotically active variant or fragment thereof.

The use of therapeutically active proteins or polypeptides was for a long time hampered by the inability of these proteins or polypeptides to cross the cell membrane barrier. The discovery of protein transduction domains (PTDs) like that from the HIT Tat protein which act as shuttle molecules facilitated the transduction of large proteins or polypeptides into the target cell. Protein transduction domains enable the PTD-protein complex to enter a cell in an receptor-independent manner. Several different PTDs have been identified so far, for example in the Antennapedia protein of Drosophila, the VP22 protein of Herpes simplex virus and the TAT protein from HIV type 1. These PTDs generally consist of about 10-50 amino acids and share several structural similarities. One striking feature of PTDs is the possession of several basic amino acids which is indicative for a general mechanism by which these molecules enter the cell. It has been speculated that an interaction of heparan structures on the surface of the target cell with the basic amino acids in the PTD sequence result finally in the transduction of the whole molecule into the cell.

As used in the context of the present invention, the term "fusion protein" refers to a non-naturally occurring hybrid protein comprising at least two different proteins or protein fragments. The fusion protein of the present invention comprises a protein transduction domain which is suitable for introducing the fusion protein into a cell, preferably into a mammalian cell of a patient which is in need of an anti-apoptotic treatment. Preferably, the patient is a human patient and the cells into which the fusion protein of the invention shall enter via the PTD is a human cell, for example, a cell of an organ tissue, such as renal tissue. In principle, any PTD may be used which does not adversely affect folding of the anti-apoptotic protein to which it is fused or otherwise coupled. This means, the PTD should not interfere with the anti-apoptotic activity of the protein comprising the amino acid sequence of SEQ ID NO:1 or an anti-apoptotically active fragment or variant thereof to an extent that the desired anti-apoptotic activity is abolished. It is understood, however, that a loss of activity of the anti-apoptotic protein of 20%, 30%, 40%, 50%, 60%, 70, or even up to 80% may be tolerated in cases where a particular fusion protein exhibits other favorable characteristics, such as an increased stability or shelf-life or improved. pharmacological properties, such as a decreased immunogenicity. The skilled person will be readily able to assess whether a given fusion protein is suitable for being used in a desired therapeutic context.

According to a preferred aspect of the invention, the protein transduction domain used in the fusion protein is derived either from the Antennapedia protein of Drosophila, the VP22 protein of Herpes simplex virus or the TAT protein from human immunodeficiency virus (HIV) type 1. According to a particularly preferred embodiment, the fusion protein comprises a protein transduction domain which is derived from the transduction domain of the Tat protein of HIV type 1. The transduction domain of the Tat protein of human immunodeficiency virus type 1 has been described in the art in several publications, for example, in Bhorade, R. et al. (2000), Bioconjug. Chem. 11:301-305; Becker-Hapak, M. et al. (2001), Methods 24:247-256; and Dietz, G. et al. (2002), Mol. Cell Neurosci. 21:29-37. Mutagenesis studies showed that a core structure of 11 amino acids of the HIV Tat transduction domain is sufficient for the efficient transfer of proteins across the cell membrane. The minimal structure of the HIV Tat transduction domain is represented by the 11-amino acid sequence YGRKKRRQRRR (SEQ ID NO:3). Thus, in a preferred embodiment, the fusion protein comprises a protein transduction domain which comprises or consists of the amino acid sequence of SEQ ID NO:3 or an amino acid sequence having at least 80%, preferably at least 95%, identity thereto.

The fusion protein of the invention also comprises, as a further component, the amino acid sequence of SEQ ID NO:1 or an anti-apoptotically active fragment or variant thereof. The amino acid sequence set forth in SEQ ID NO:1 describes the primary structure of the cytokine response modifier A (CrmA) protein from the cowpox virus. This protein has been shown to be an efficient suppressor of apoptosis. By developing an anti-apoptotic protein during evolution, the cowpox virus has gained the ability to protect the host cells which are used by the virus for propagation. Unlike other apoptosis suppressors, the effect of CrmA is based on the simultaneous inhibition of caspases-1 and -8 of the extrinsic pathway, caspase-9 of the intrinsic pathway, and executor caspases-3, -6 and -7. Due to this manfold mode of action, CrmA is a particularly powerful inhibitor of apoptosis.

Several attempts have been made in the art to use the CrmA protein for blocking apoptosis both in in vitro systems and in animal models. These attempts were based on the heterologous expression of the CrmA protein in cell lines or transgenic animals, which has the fundamental disadvantage that CrmA expression cannot be shut off once the expression construct has been introduced into the target cell. The particular advantage of the present invention resides in the fact that the inhibition of an undesired apoptosis is feasible for a limited period of time. The fusion protein of the invention allows for the temporary inhibition of apoptosis in situations where transient suppression of cell death is desired. It has been shown that the fusion proteins of the invention exhibit a half life time of approximately 8 hours, so that the extent and duration of treatment can be readily adjusted by the frequency of administration of the fusion protein. In other words, the introduction of the CrmA protein by use of a protein transduction domain enables the practitioner to adjust the anti-apoptotic treatment to the clinical situation of the patient to be treated.

As will be appreciated by the person of skill, the cowpox virus is subject to permanent modification due to the high mutation rate of the viral genome. As a consequence, several amino acid sequences are available in the databases for the CrmA protein which differ one or more amino acids from the amino acid sequence in SEQ ID NO:1. These variants of CrmA are comprised by the present invention provided that they have an anti-apoptotic activity. As used herein, variants of the protein of SEQ ID NO:1 are proteins with an amino acid sequence that differs from the amino acid sequence of the protein of SEQ ID NO:1 by one or more amino acid substitutions, additions or deletions. In general, any amino acid residue of the sequence shown in SEQ ID NO:1 may be substituted by another amino acid, provided that the resulting protein variant still exhibits an anti-apoptotic activity. Determination of the anti-apoptotic activity can be performed, for example, by the method described in Wender et al. (2000),*Proc. Natl. Acad. Sci USA* 97 (24):13003-8. In particular, protein variants are included which differ from the amino acid sequence shown in SEQ ID NO:1 in up to 5, 10, 15, 20 or even up to 25 amino acid positions.

It is preferred that the substitutions are conservative substitutions, i.e. substitutions of an amino acid residue by another amino acid of a similar polarity, which acts as a functional equivalent. Preferably, the amino acid residue used as a substitute is selected from the same group of amino acids as the amino acid residue to be substituted. For example, a hydrophobic residue can be substituted with another hydrophobic residue, or a polar residue can be substituted with another polar residue having the same charge. Functionally homologous amino acids which may be used for a conservative substitution comprise, for example, non-polar amino acids such as glycine, valine, alanine, isoleucine, leucine, methionine, proline, phenylalanine, and tryptophan. Examples of uncharged polar amino acids comprise serine, threonine, glutamine, asparagine, tyrosine and cysteine. Examples of charged polar (basic) amino acids comprise histidine, arginine and lysine. Examples of charged polar (acidic) amino acids comprise aspartic acid and glutamic acid.

Also comprised by the term "variant" are protein sequences which include more amino acids than the sequence of SEQ ID NO:1, i.e. protein sequences in which one or more amino acids have been inserted. Such insertions may in principle occur at any position of the protein of SEQ ID NO:1. The insertions may be stretches of contiguous amino acids comprising, for example, 2, 3, 4, 5, 6, 7, 8, 9 or ten amino acids. Similarly, the term "variant" also includes protein sequences in which one or more amino acids are deleted as compared to the protein of SEQ ID NO:1. The deletion can involve several contiguous amino acid residues of the protein of SEQ ID NO:1, for example, 2, 3, 4, 5, 6, 7, 8, 9 or ten amino acids. A particular preferred variant of the CrmA protein has the amino acid sequence shown in SEQ ID NO:2, This variant inter alia differs from the CrmA protein of SEQ ID NO:1 by lack of the valine-serine-alanine stretch shown in positions 55-57 of SEQ ID NO:1. This deletion does not affect the anti-apoptotic activity of the variant. Variants of the protein of SEQ ID NO:1, also include structural modifications, for example modified amino acids, such as amino acids that have been altered by phosphorylation, glycosylation, acetylation, thiolation, branching and/or cyclization.

The variants of the CrmA protein of SEQ ID NO:1, which have been modified by substitution, addition or deletion of amino acids, normally show a considerable degree of amino acid sequence homology or identity to the CrmA protein of SEQ ID NO:1. Preferably, the homology or identity on the amino acid level is at least 70%, 75%, 80%, 85%, 90%, 91%, 92%, 93%, 94%, 95%, 96%, 97%, 98% or 99% if the sequence of the variant is optimally aligned with that of SEQ ID NO:1. Methods and computer programs for determining amino acid homology are well known in the art.

The present invention also contemplates the use of anti-apoptotically active fragments, which are either derived from the protein of SEQ ID NO:1 or its variants. Anti-apoptotically active fragments of SEQ ID NO:1 or its variants include peptides or polypeptides that differ from the amino acid sequence shown in SEQ ID NO:1 or from its variants by the absence of one or more amino acids at the N-terminus and/or C-terminus of the protein. For example, the CrmA component of the fusion protein used in the below examples lacks the methionin residue in position 1 of the sequence depicted in SEQ ID NO:1, which means that it actually represents a fragment of the sequence in SEQ ID NO:1. The person of ordinary skill will be able to determine further active fragments of the sequence depicted in SEQ ID NO:1 or its variants by performing routine methods described in great detail in the prior art.

Preferably, the fusion protein of the invention further comprises a linker between the protein transduction domain and the anti-apoptotic protein. The linker may comprise any number of amino acids as long as the anti-apoptotic activity of the CrmA portion is maintained and the introduction of the fusion protein into the cell via the PTD is still effected. The linker normally comprises 5-30 amino acids, preferably 8-25 amino acids, and more preferably 10-20 amino acids. The linker regularly includes several glycine residues, since this amino acid is less likely to affect protein folding of the active portion of the fusion protein. The fusion protein may also comprise additional components, for example, an affinity tag which facilitates binding of the fusion protein via a compound exhibiting binding affinity to the tag. For example, the affinity tag may be a poly-histidine tag comprising 6-12 histidine residues which specifically interacts with a nickel ion chelate matrix. The fusion protein which was used in the examples of the present invention (designated TAT-CrmA) and which is depicted in SEQ ID NO:4 comprises a tag of 6 histidine residues for purification. Alternatively, the tag may be glutathione-S-transferase allowing the purification on a glutathione matrix. Further affinity tags are well-known in the art. Non-liming examples for pairs of affinity tag and affinity ligand include maltose-binding-protein (MBP) and maltose; avidin and biotin; Streptag and streptavidin or neutravidin. Affinity tags may be attached to a molecule by fusion/ligation of cDNAs of the molecule of interest with the sequence encoding the tag. Where the affinity tag is a peptide or polypeptide, such tag may conveniently be expressed together with the fusion protein of the invention as a single expression product. In other embodiments, the affinity tag may be attached by chemical coupling reactions. For example, biotin may be chemically coupled to the fusion protein.

The fusion protein of the invention has been shown to be effective in inhibiting or blocking apoptosis when administered in the form suitable for the delivery of therapeutic proteins. Accordingly, the fusion protein provided by the invention is for blocking apoptosis in a patient in need thereof. The fusion protein may be used, for example, for treating diseases which involve a dysregulated, excessive level of apoptosis, such as reperfusion injury, stroke, myocardial infarction, toxic and ischemic organ failure, fulminant hepatic failure, AIDS, neurodegenerative diseases, graft versus host disease, alcoholinduced liver cirrhosis, spinal cord injury, acute leukemia, or viral hepatitis.

Preferably, the fusion protein of the present invention is administered as a pharmaceutical composition. Accordingly, the invention also provides a pharmaceutical composition comprising a fusion protein as defined above. The pharmaceutical composition is for blocking apoptosis in a patient in need thereof. In particular, the composition is for treating reperfusion injury, stroke, myocardial infarction, toxic and ischemic organ failure, fulminant hepatic failure, AIDS, neurodegenerative diseases, graft versus host disease, alcohol induced liver cirrhosis, spinal cord injury, acute leukemia or viral hepatitis. The preparation of pharmaceutical compositions comprising one or more therapeutic proteins is well known by those working in the field of pharmaceutics. Typically, such compositions are prepared for injection either as liquid solutions or suspensions. The active ingredient (i.e. the fusion protein) can be mixed with excipients which are pharmaceutically acceptable and compatible with the fusion protein when used in human patients. The pharmaceutical compositions of the present invention normally comprise a physiologically acceptable carrier together with the fusion protein dissolved or dispersed therein as an active ingredient. Pharmaceutically acceptable carriers comprise, for example, water, saline, Ringer's Solutions, or dextrose solution. Further suitable carriers for compositions comprising the anti-apoptotic fusion protein of the invention are described in standard textbooks, for example, in "Remington's Pharmaceutical Sciences", Mack Pub. Co., New Jersey (1991). In addition to a carrier, the pharmaceutical composition of the invention may also comprise wetting agents, buffering agents, stabilizers, dyes, preservatives and the like in any concentration, provided that these compounds do not interfere with the anti-apoptotic activity of the fusion protein of the invention.

Different routes of administration are feasible for providing the fusion protein to the site or organ which requires the inhibition of apoptosis. Preferably, the pharmaceutical composition is formulated for systemic administration, for example, for parenteral administration. Parenteral administration may include intravenous, intradermal, intraarterial, subcutaneous, topical, transmucosal, or rectal administration. According to a particular preferred embodiment, the pharmaceutical composition is formulated for injection.

Pharmaceutical compositions suitable for injection normally include sterile aqueous solutions or dispersions and sterile powders for the extemporaneous preparation of sterile injectable solutions or dispersion. The composition should furthermore be stable under regular conditions of manufacturing and storage. The composition intended for injection must be sterile in order to avoid a severe immunologic reaction in the patient receiving the injection. For maintaining sterility, the pharmaceutical composition normally includes preservatives, such as parabens, chlorobutanol, phenol, ascorbic acid, thimerosal, and the like, to suppress microbial growth in the product. For intravenous or intraarterial administration, suitable carriers may comprise physiological saline, bacterio-static water, Cremophor EL™ (BASF) or phosphate buffered saline (PBS). The carrier may also be a solvent or dispersion medium containing, for example, water, ethanol, polyol (for example, glycerol, propylene glycol, and liquid polyethylene glycol, and the like), and suitable mixtures thereof. A prolonged absorption of the injectable compositions can be achieved by including into the composition an agent which delays absorption, for example, aluminum monostearate or gelain. Sterile injectable solutions can be prepared by incorporating the active ingredient (the fusion protein) in the required amount in an appropriate solvent with one or a combination of the above mentioned ingredients followed by sterile filtration. Similarly, dispersions are prepared by incorporating the fusion protein into a sterile vehicle that contains a dispersion medium and optionally other ingredients as outlined above. Sterile solutions can also be obtained by providing the fusion protein in the form of a sterile powder by methods known in the art, such as vacuum drying or freeze-drying, and reconstituting the powder with a sterile liquid to yield the final solution for injection. Alternatively, the pharmaceutical composition according to the invention may also be administered by continuous infusion.

Administration of the pharmaceutical composition may also be achieved by transmucosal or transdermal delivery. For transmucosal or transdermal administration, the pharmaceutical composition comprising the fusion protein of the invention will comprise penetrants which are appropriate for crossing the skin or mucosal barrier. Such penetrants are known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. Preferably, the compounds are prepared in the form of suppositories, with conventional suppository bases such as cocoa butter and other glycerides for rectal delivery.

In one embodiment, the active compounds are prepared with carriers that will protect the peptides against elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparing controlled release formulation are well-known in the art. Furthermore, sustained-release compositions may be prepared. Suitable examples of sustained-release preparations include semipermeable matrices of solid hydrophobic polymers, which matrices are in the form of shaped articles, e.g., films or microcapsules. Examples of sustained-release matrices include polyesters, hydrogels, polylactides, copolymers of L-glutamic acid and ethyl-L-glutamate, non-degradable ethylene-vinyl acetate, degradable lactic acid-glycolic acid copolymers and the like.

In a further aspect, the present invention provides a method of treating a pathological apoptosis in a patient in need thereof comprising the administration of a therapeutically effective amount of an anti-apoptotic fusion protein as defined above. Preferably, the patient is suffering from a disease which involves a dysregulated, excessive level of apoptosis, such as reperfusion injury, stroke, myocardial infarction, toxic and ischemic organ failure, fulminant hepatic failure, AIDS, neurodegenerative diseases, graft versus host disease, alcohol-induced liver cirrhosis, spinal cord injury, acute leukemia, or viral hepatitis.

A therapeutically effective amount of the anti-apoptotic fusion protein is typically an amount which—upon administration—is sufficient to effectively block or inhibit apoptosis in the target organ or tissue of the patient to be treated. Typically, the dosage of the fusion protein per body weight varies from about 0.1 mg per kg body weight of the patient to about 50 mg per kg body weight of the patient, and more preferably from about 0.5 mg per kg body weight of the patient to about 20 mg per kg body weight of the patient, and even more preferably from 1 mg per kg body weight of the patient to about 10 mg per kg body weight of the patient. The administration regimen may include one or more administrations of the protein daily. It will be appreciated by those skilled in the art that the concrete amount of the fusion protein which is to be administered to the patient will depend on several factors, such as age and weight of the patient, as well as from the nature and severity of the medical symptoms to be treated. The amount which exerts the desired therapeutic effect may be determined in each individual case by use of routine experimentation.

In a further aspect, the invention relates to a polynucleotide encoding a fusion protein as defined above. Polynucleotides which encode the fusion proteins of the invention may consist of DNA or RNA. The polynucleotide encoding the fusion protein of the invention refers to a DNA or RNA molecule which directs the expression of the desired fusion protein. An exemplary polynucleotide which codes for a fusion protein of the invention is depicted in SEQ ID NO:5; this polynucleotide encodes the TAT-CrmA fusion protein of SEQ ID NO:4. However, it is to be understood that other polynucleotides encoding the protein of SEQ ID NO:1, which differ from the sequence of SEQ ID NO:5 in one or more of the nucleotide position due to the degeneracy of the genetic code, are also included. Similarly, polynucleotides encoding variants or fragments of the protein of SEQ ID NO:1 are also included.

The polynucleotides encoding the fusion proteins of the invention may be cloned in an expression vector in order to provide means for recombinant preparation the fusion protein. Generally, expression vectors are self-replicating DNA or RNA constructs into which a polynucleotide of interest is inserted such that the coding sequence of the polynucleotide is operably linked to suitable regulatory elements which allow for the controlled expression of the coding sequence in a host cell. The specific control elements which are required for expression of the polynucleotide will depend on the host cell that is used and may include a transcriptional promoter, an operator, an enhancer to increase the mRNA expression level, a ribosome binding site, and suitable transcription and translation terminators. The promoter can be a constitutive or inducible promoter, for example, the commonly used promoters of galactokinase, uridylyltransferase, phosphoglycerate kinase, glyceraldehyde-3-phosphate dehydrogenase, alcohol dehydrogenase, or viral promoters, such as the promoters from SV40, cytomegalovirus (CMV) or Molony murine leukemia virus (MMLV), and the like. Expression vectors may also contain an origin of replication for the autonomous replication of the vector within a host cell, and one or more selection marker which allow monitoring the transfection into the host cell.

The expression vector may be designed for expressing the recombinant protein in a prokaryotic or eukaryotic host. Preferably, the expression vector will nave one capability to stably replicate within the host cell so that the number of the polynucleotide which encodes the fusion protein of interest is increased within the cell. It as, however, also possible to use an expression vector which is unable to replicate within the cells and allows only transient expression of the fusion protein. Alternatively, expression vectors may be used which integrate into the genome of the host cell that is transduced or transfected with the expression vector. Various expression vectors are known in the prior art which are suitable for mediating expression of the anti-apoptotic fusion protein of the invention both in prokaryotic or eukaryotic host cells. Methods for introducing the expression vector into a host cell have also been extensively discussed in the literature. A variety of different methods may be used for transducing or transfecting the expression vector of the invention into a host cell, for example, electroporation, microinjection, transformation, transfection, protoplast fusion, microprojectile bombardment and the like.

Accordingly, the invention also relates to a host cell which comprises an expression vector harboring a polynucleotide encoding the fusion protein of the invention. The cells may be derived from prokaryotes, or from lower or higher eukaryotes. Suitable prokaryotes which can be transduced or transfected with an expression vector encoding the fusion protein of the invention include, for example, bacteria like *Bacillus subtilis, Escherichia coli*, and the like. Lower eukaryotes that may be used in the methods of the present invention include yeasts, in particular yeasts of the genus *Saccharomyces*, such as *S. cerevisiae, S. bailii, S. bayanus, S. boulardii, S. carlsbergensis*, of the genus *Pichia*, such as *P. pastoris, P. methanolica, P. stipitis*, or of the genus *Dictyostelium*, such as *D. discoideum*. Higher eukaryotes include animal cell lines, in particular mammalian cell lines, for example cell lines derived from rodents, primates and human. Useful cell lines for use according to the invention include Chinese hamster ovary (CHO) cell lines, baby rat kidney (BRK) cell lines, Madin Darby canine kidney (MDCK) cell lines, NSO myeloma cells, monkey kidney COS cells, human embryonic kidney 293 cells, and cancer cell lines such as SKBR3 cells, Jurket T cells or HeLa cells.

The host cells of the invention which comprise a polynucleotide encoding the anti-apoptotic fusion protein of the invention, preferably in the form of an expression vector suitable of directing expression in the respective host cell, may be conveniently used for preparing the fusion protein. Preferably, the expression vector is introduced into the host cell such that the expression of the fusion protein is effected by propagation of the host cells. Accordingly, the invention also provides a method for preparing a fusion protein as defined herein, comprising the culturing of a host cell which comprises the polynucleotide encoding the anti-apoptotic fusion protein or the expression vector including such polynucleotide under conditions which allow for the expression of the fusion protein.

The provision of the fusion proteins of the invention allows for the preparation of antibodies which hand to said fusion protein. The method comprises the immunization of a non-human animal with the fusion protein, and obtaining the antibodies produced in response to the fusion protein from the serum of said animal.

The invention therefore also relates to the use of a fusion protein as defined herein or a polynucleotide encoding such fusion protein for the preparation of a pharmaceutical composition for blocking apoptosis in a patient in need thereof. Similarly, the invention also relates to the use of an expression vector comprising a polynucleotide encoding a fusion protein of the invention and to a host cell comprising such a polynucleotide or expression vector for the preparation of a pharmaceutical composition for blocking apoptosis in a patient in need thereof. Preferably, these materials are for the preparation of a pharmaceutical composition for the treatment of reperfusion injury, stroke, myocardial infarction, toxic and ischemic organ failure, fulminant hepatic failure, AIDS, neurodegenerative diseases, graft versus host disease, alcohol induced liver cirrhosis, spinal cord injury, acute leukemia, or viral hepatitis.

Finally, the invention also contemplates a kit comprising the fusion protein of the invention, a polynucleotide encoding such fusion protein, an expression vector comprising a polynucleotide encoding such fusion protein and/or a host cell comprising such a polynucleotide or expression vector. The kit may comprise further materials which are useful for preparing a composition for administration to the patient. For example, the kit may include buffers, stabilizers, carriers and the like for mixing with the fusion protein prior to administration. The kit will further comprise instructions for using the components in the preparation of a pharmaceutical composition for blocking apoptosis in a patient suffering from an increased or dysregulated level of apoptosis. For example, the instructions will relate to the administration of the fusion protein to a patient, for example, in preferred dosage regimens. If the kit comprises an expression vector harboring a polynucleotide coding for the fusion protein of the invention, the instructions will further relate to the introduction of said vector into a suitable host cell and to conditions suitable for expressing and recovering the fusion protein of the invention.

EXAMPLES

Example 1

Cloning and Expression of TAT-CrmA

Total RNA was isolated from a human skin lesions caused by cowpox virus by using RNeasy minicolumns (Qiagen, Hilden, Germany). cDNA was generated by using Thermoscript RT-PCR System (Invitrogen, Karlsruhe, Germany) with the forward primer (5'-CCGGGTACCGATATCTTCA-GGGAAATCGCATC-3', SEQ ID NC: 6) and reverse primer (5'-CCGGAATTCTTAATTAGTTGTTGGAGAG-CAATATCTA-3', SEQ ID NO:7). The PCR product was cloned into the KpnI/EcoRI-cut pTAT-vector. A vector was constructed based on pRSE (Invitrogen). This vector contains a 6-histidine leader for pulification and a multiple cloning site. In this vector the coding sequence for the 11-amino acid TAT protein transduction domain (see Green, M. and Loewenstein, P. M. (1988), Cell 55:1179-1188) was inserted.

The resulting plasmid of a selected colony harbouring the cDNA of TAT-CrmA was transformed into competent T7 Express I$^q$ E. coli bacteria (New England BioLabs), followed by induction of expression in LB media with isopropyle-β-D-thiogalacto-pyranoside (final concentration of 0.4 mM). After 2 hours of induction at 37° C. cells were harvested by centrifugation (6,500×g, 10 min, 4° C.) followed by sonification in binding buffer (500 mM NaCl, 20 mM Tris-HCl, 5 mM imidazole, pH 7, 9).

Example 2

Purification of TAT-CrmA

The suspensions obtained according to Example 1 were clarified by centrifugation (14,000×g, 20 min, 4° C.) and the supernatants containing the fusion proteins were purified under native conditions using pre-equilibrated Ni-NTA columns (Qiagen, Hilden, Germany). To remove high background of contaminating bacterial proteins columns were washed by stepwise addition of increasing imidazole concentrations. Finally, the target proteins were eluted with an elution buffer containing 500 mM NaCl, 20 mM Tris-HCl and 100 mM imidazole (pH 7, 9). Removal of salt has been performed using a disposable PD-10 (Sephadex G-25) desalting column equilibrated in RPMI medium. The fusion proteins were either used immediately after purification or stored at +4° C. or −20°.

Example 3

Spectrofluorometric Analysis of Caspase Activity

Human T lymphocytic Jurkat cells were cultured in RPMI medium supplemented with 10% FCS and penicillin-streptomycin. For the experiments, the cells were seeded at a density of $1.0×10^6$ cells/ml. The cells were either left untreated (A), were treated with 100 ng/ml anti-Fas antibody (clone 7C11, Immunotech) alone (B) or were treated for 30 min with 500 nM TAT-CrmA prior to the addition of the anti-Fas antibody (C). Stimulation of the cells was terminated by aspirating the medium and washing the cells twice with ice-cold PBS. Cells were subsequently resuspended in cold cell lysis buffer (BD Biosciences) and incubated for 30 min on ice. The cell lysates were then incubated with caspase-3 substrate Ac-DEVD-AMC (Ac-aspartyl-glutamyl-valyl-aspartyl-aminomethylcoumarin) alone or with the substrate and the specific caspase-3 inhibitor Ac-DEVD-CHO and analyzed by spectrofluorometry. For each reaction 5 μl reconstituted caspase-3 substrate alone (black) or substrate and the caspase-3 inhibitor (white) were added to 50 μl cell lysate and incubated for 1 hr at 37° C. The amount of AMC released from Ac-DEVD-AMC was measured by using a plate reader (Infinite M200, Pecan) with an excitation wavelength of 380 nm and an emission wavelength of 440 nm.

The results are shown in FIG. 1. Fluorescence was not emitted in lysates of cells treated with both the inhibitor Ac-DEVD-CHO and the caspase-3 substrate Ac-DEVD-AMC, indicating that caspase-3 activity was blocked (white boxes). In the untreated cells (A), there was also no significant fluorescence detected in cells incubated only with Ac-DEVD-AMC but no inhibitor (black box), indicating that caspase-3 was not active in these cells. In contrast, cells treated with anti-Fas antibody (B), a remarkable release of aminomethylcoumarin-related fluorescence was detected in cells incubated only with Ac-DEVD-AMC (black box), demonstrating that caspase-3 was active. In cells treated with anti-Fas antibody and fusion protein TAT-CrmA (C), aminomethylcoumarin-related fluorescence was considerably reduced compared to (B). This shows that preincubation of cells with fusion protein TAT-CrmA inhibits the activity of caspase-3, thereby leading to a decreased extent of apoptosis.

Example 4

Determination of Mitochondrial Membrane Potential

Detection of the mitochondrial permeability transition event, an early indication of cellular apoptosis, was measured by the change in the membrane potential ($\Delta\psi$) using the Mito-PT™ Kit (Immunochemistry Technologies, LLC). This kit allows distinction between non-apoptotic (red fluorescence) and apoptotic (green fluorescence) cells and was used according to manufacturer's instructions.

$2×10^6$ Jurkat T cells per reaction were treated with DMSO (negative, non-induced cells), with 2,5 μM Staurosporine or with 100 ng/ml anti-Fas antibody (apoptotic, induced cells) for 4 hours at 37° C. and then labeled with 1× MitoPT™ solution for 15 minutes. For the induced cells, parallel reactions were prepared which were treated by adding 500 nM TAT-CrmA prior to the addition of Staurosporine or anti-Fas antibody, respectively. Incubation and labeling were performed as described above (4 hours at 37° C., labeling with 1× MitoPT™ solution for 15 minutes). Collapse of the mitochondrial $\Delta\psi$ was measured by using plate reader (Infinite M200, Tecan) with an excitation wavelength of 490 nm and an emission wavelength of 600 nm. The experiments were performed in triplicate.

Figure 2:
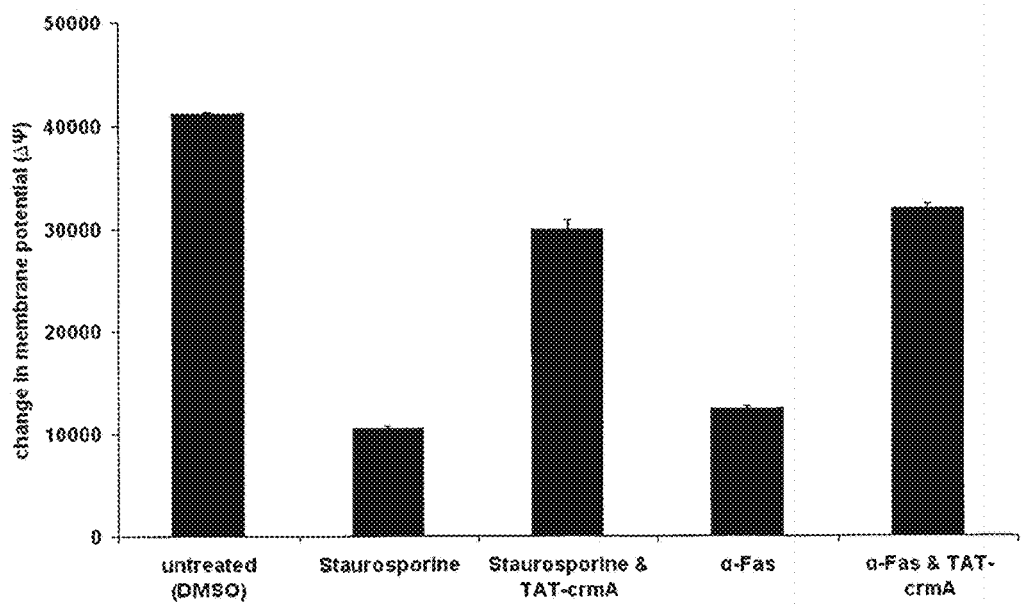
FIG. 2 shows the determination of apoptosis as measured by the change in membrane potential. Treatment of the cells with fusion protein TAT-CrmA prior to the addition of Staurosporine or anti-Fas antibody, respectively, partially abrogated the loss of membrane potential in the cells induced by these both stimuli.

The results are shown in FIG. 2. It can be seen that the addition of the fusion protein TAT-CrmA prior to the addition of Staurosporine or anti-Fas antibody, respectively, abrogated the loss of membrane potential that was observed in cells which were only treated with the apoptosis-inducing Staurosporine or anti-Fas antibody.

Example 5

Annexin V-Staining

Apoptosis was also quantified by FACS analysis using FITC-labeled Annexin V. The protein Annexin V binds to phosphatidyl serine residues which are exposed on the cell surface at an early stage of apoptosis. Jurkat cells were incubated either for 30 min with 500 nM TAT-CrmA followed by addition of anti-Fas antibody for 4 hrs at 37° C. (A) or were left untreated by incubation for 4 hrs at 37° C. with vehicle (B) or were incubated with 100 ng/ml anti-Fas antibody (clone 7C11, Immunotech) for 4 hrs at 37° C. (C). After stimulation cells were harvested, washed with RPMI supplemented with 2% FCS and Annexin V-staining (ApoAlert, Annexin V-FITC, BD Biosciences, Heidelberg, Germany) was performed according to the manufacturer's instructions. Fluorescence was analyzed by an EPICS XL® (Coulter, Krefeld, Germany). Flow cytometry data were analyzed using the EPICS System II software.

Figure 3:
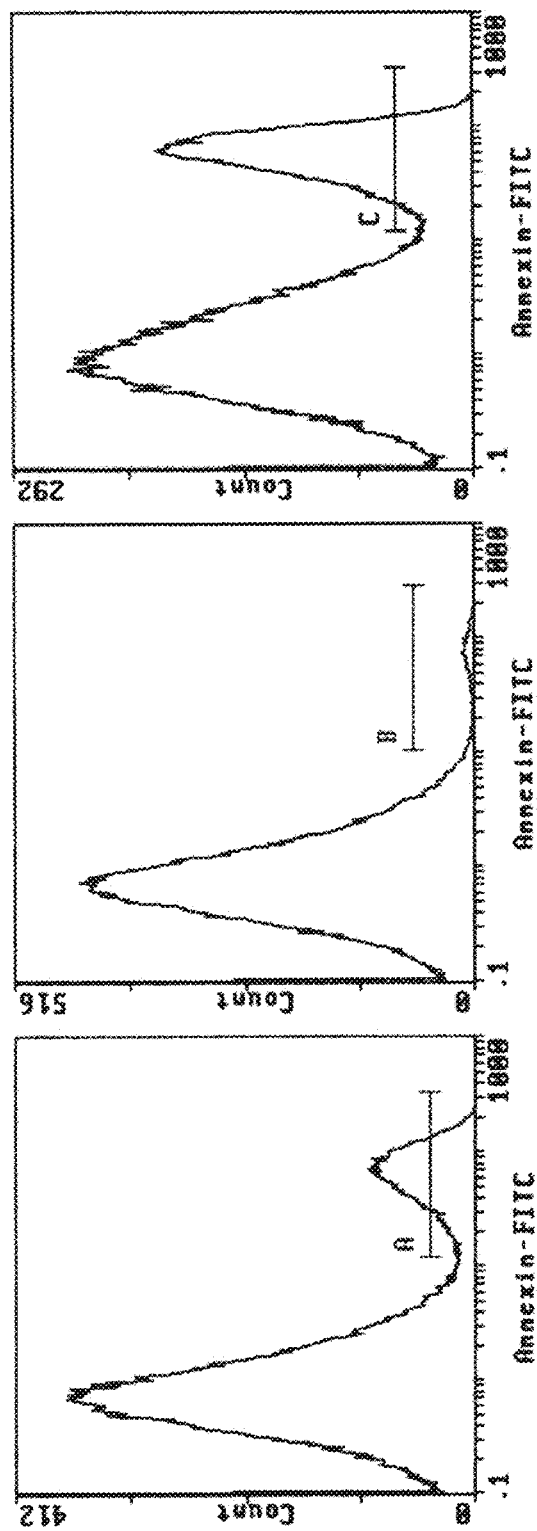
FIG. 3 shows the detection of apoptosis by FACS analysis using FITC-labeled Annexin V in Jurkat cells that were incubated with TAT-CrmA and anti-Fas antibody (A), in untreated Jurkat cells (B) or in Jurkat cells that were incubated only with anti-Fas antibody (C). The number of cells undergoing apoptosis is significantly reduced in reactions using TAT-CrmA compared to reactions using only anti-Fas antibody.

The graphs depicted in FIG. 3 show the result of a single representative experiment. It can be seen that the number of cells undergoing apoptosis is significantly reduced in reactions using anti-Fas antibody and TAT-CrmA (A) as compared to reactions using only anti-Fas antibody (C). 4 hours after stimulation with α-Fas, cells additionally incubated with 500 nM TAT-CrmA were protected from extrinsic apoptosis as determined by 80% reduction of positive Annexin-V staining.

Example 6

Anti-Fas Antibody-Mediated Apoptosis in vivo

Female Balb/c mice were obtained from Charles River (Sulzfeld, Germany) and used for experiments at 6 to 8 weeks of age. In order to evaluate the extrinsic apoptotic pathway in vivo, apoptosis was induced by intraperitoneal injection of 1 mg/kg body weight monoclonal agonistic α-Fas antibody Jo-2 (BD Pharmingen). This antibody induces apoptosis in Fas-positive cells and results in a multi-organ failure in the mice. For survival studies two groups of mice (10 animals/group) received anti-Fas antibody Jo-2 alone or in combination with 7.5 mg/kg body weight TAT-CrmA. TAT-CrmA was given twenty and five minutes before α-Fas injection.

For histological analysis mice were sacrificed 5 or 8 hours after application of α-Fas. Sections were acetone-fixed, stained with haematoxylin-eosin and examined by light microscopy at 200× and 400× magnification. Apoptotic cells were identified in paraformaldehyde-fixed organ sections (5 μm) using terminal deoxynucleotidyl transferase-mediated dUTP nick end labelling (TUNEL, In situ cell death detection kit, TMR red; Roche Molecular Biochemicals, Mannheim, Germany). Staining was performed according to the manufacturer's instructions. TUNEL-positive cells were visualized by fluorescent microscopy at 200× and 400× magnification. Nuclei were counter-stained with DAPI (Dianova, Hamburg, Germany).

Figure 4:
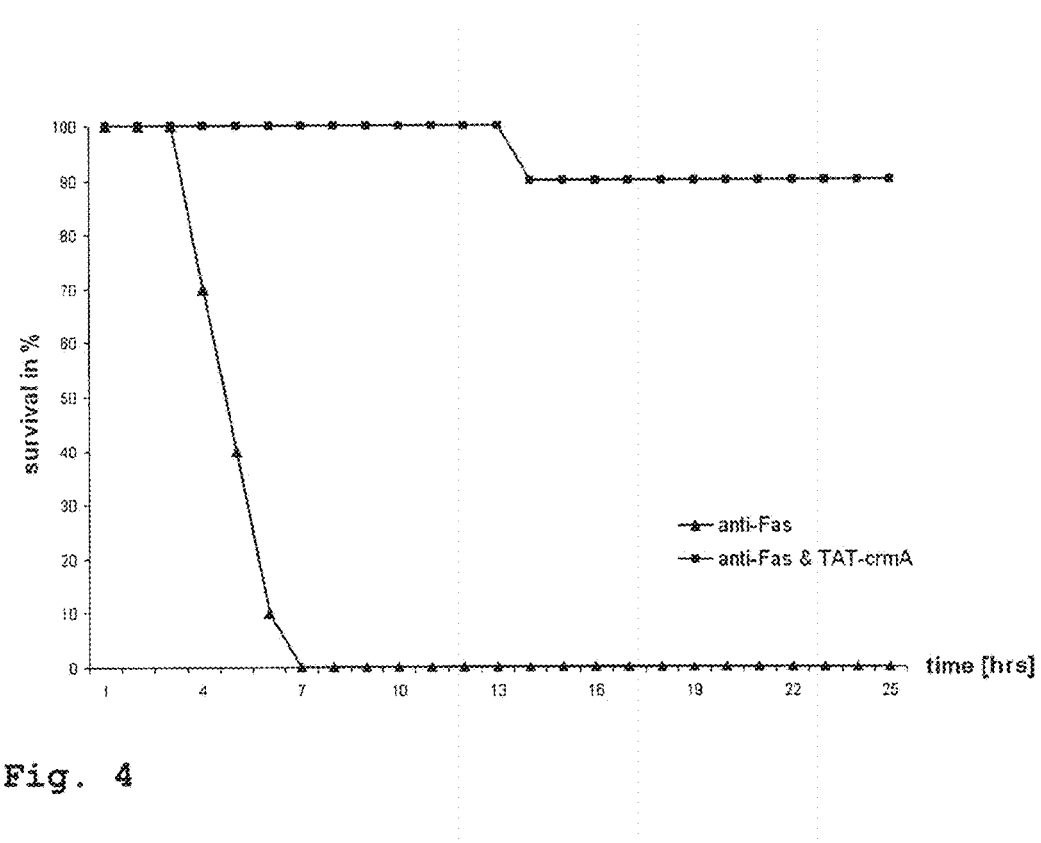
FIG. 4 depicts the results of in vivo studies in mice using the fusion protein TAT-CrmA. The fusion protein effectively protects mice from Fas-mediated apoptosis in vivo.

The cumulative survival of mice receiving α-Fas antibodies plus TAT-CrmA was significantly better compared to mice receiving α-Fas mAb alone (FIG. 4). 90% of mice receiving α-Fas mAb and TAT-CrmA survived more than 3 months (shown is the first day) whereas all mice of the α-Fas group died during the first 10 hours. None of the mice treated with TAT-CrmA alone showed any toxic effects.

Macroscopically, the liver appeared dark brown in α-Fas-treated animals, but concomitant treatment with TAT-CrmA preserved the normal aspect of the liver compared to controls. The severe structural liver damage was confirmed by histological evaluation. 5 and 8 hours after α-Fas treatment the HE-stained liver tissue exhibited severe liver cell death that was prevented by the addition of TAT-CrmA. TUNEL-staining revealed the absence of apoptosis in the TAT-CrmA-treated animals. These results show that the fusion protein of the present invention is capable of protecting mice from anti-Fas antibody-induced apoptosis in vivo Example 7

Doxorubicin-Mediated Apoptosis in vivo

Female Balb/c mice were obtained from Charles River (Sulzfeld, Germany) and used for experiments at 6 to 8 weeks of age. Apoptosis was induced by intraperitoneal injection of doxorubicin. The DNA-damaging topoisomerase inhibitor doxorubicin induces the intrinsic pathway of apoptosis. For survival studies two groups of mice (5 animals/group) were treated with a single injection of 15 mg/kg body weight doxorubicin i.p. with and without two applications of 150 μg TAT-CrmA. TAT-CrmA was given twenty and five minutes before doxorubicin injection.

Figure 5:
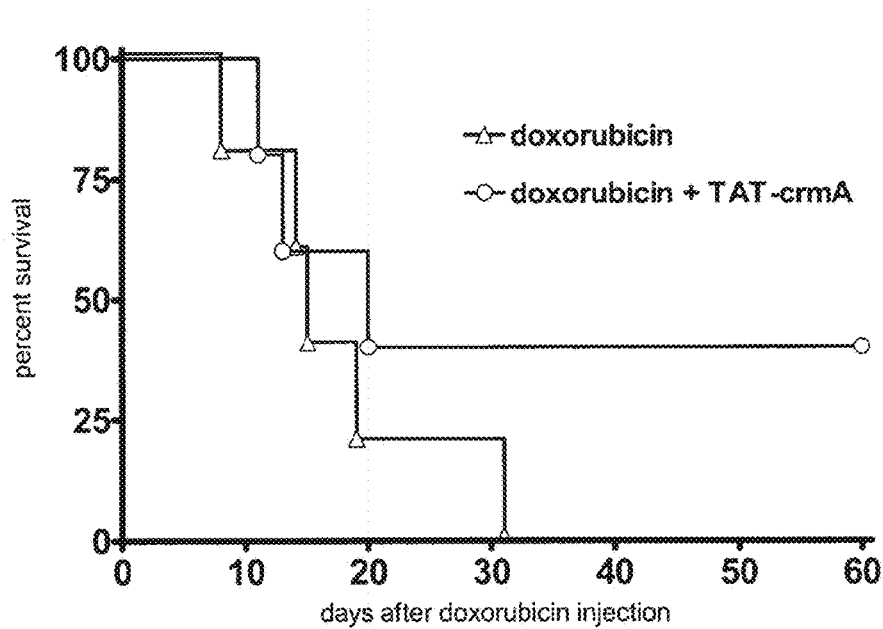
FIG. 5 depicts the results of in vivo studies in mice receiving the fusion protein TAT-CrmA. The fusion protein effectively protects mice from doxorubicin-induced apoptosis in vivo.

Survival after the otherwise lethal doxorubicin injection was prolonged through semi-daily application of TAT-CrmA for the first 7 days (FIG. 5). While all doxorubicin-treated mice died within 31 days, 40% survival was registered in mice that concomitantly received intraperitoneal injections of TAT-CrmA (n=5, p<0.05) (FIG. 5). Organ failure of doxorubicin-treated mice was prevented by TAT-CrmA. Taken together, these results provide evidence for efficient inhibition of both the intrinsic and extrinsic apoptotic pathway through TAT-CrmA fusion protein in vitro and in vivo.

Example 8

TAT-CrmA Reduces Infarction Size and Improves Systolic Function after Myocardial Infarction in Mice Since apoptosis a major pathophysiological event in ischemic tissues, TAT-CrmA was tested in a mouse model of myocardial infarction. 12 week old male C57BL/6 mice were anesthetized with ketamine hydrochloride (100 mg/kg, i.p.) and xylazine (4 mg/kg, i.p.). After tracheal intubation, anesthesia was maintained with 2% isoflurane. Mice underwent transient coronary artery ligation for 1 hour followed by reperfusion for 24 hours. Area at risk and infarction sizes were determined by Evans blue and TTC staining and computerized planimetry as described in Kempf, T., et al. (2006), Circ. Res. 98: 351-360. Transthoracic echocardiography was performed with a linear 15-MHz transducer in mice sedated with 2% isoflurane. Long-axis images [to determine left ventricular end-diastolic volume (LVEDV) and left ventricular end-systolic volume (LVESV)] and M-mode tracings were recorded. Ejection fraction was calculated in percent as $[(LVEDV-LVESV)/LVEDV] \times 100$.

Figure 6:
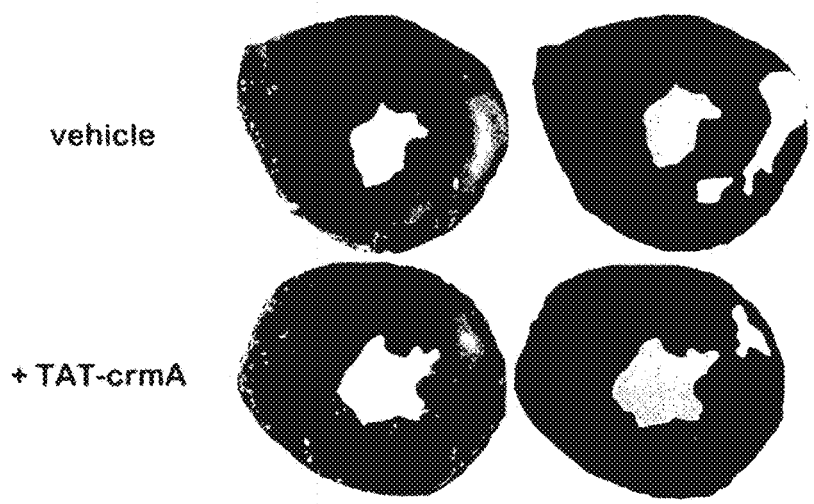
FIG. 6 shows a comparison of infarction sizes after reperfusion as determined by Evans blue and TTC staining.

C57BL/6 mice were treated with 7.5 mg/kg body weight TAT-CrmA i.p. prior to ligation of the left anterior descending artery (LAD). Ligation for 1 h was followed by reperfusion for 24 hours. The area at risk during coronary occlusion was comparable in vehicle treated ($30.5 \pm 4.2$ mm$^2$) and TAT-CrmA-treated mice ($32.8 \pm 9.1$ mm$^2$). In contrast, the infarct sizes after reperfusion were significantly larger in vehicle vs. TAT-CrmA-treated mice ($11.6 \pm 2.8$ mm$^2$ vs. $7.0 \pm 2.0$ mm$^2$, p<0.05) as determined by Evans blue and TTC staining (FIG. 6). As measured by echocardiography, the ejection fraction in sham-operated mice was $71.0 \pm 3.7\%$. After reperfusion, the ejection fraction in TAT-CrmA-treated mice ($50.7 \pm 4.9\%$) was significantly less reduced compared with vehicle treated mice ($22.6 \pm 1.7\%$, p<0.001). Subsequently, the therapeutical efficacy of TAT-CrmA when applied at the time of reperfusion after one hour of ischemia was analyzed in the same setting. Again, infarct size could be reduced about 40% when TAT-CrmA was administered with the initiation of reperfusion (Table 1). Those mice displayed an ejection fraction of $39.3 \pm 4.2\%$ compared to $23.2 \pm 4.9\%$ in vehicle treated mice, corresponding to a significantly reduced left ventricular end-systolic volume in the TAT-CrmA-treated group. Hematoxylin-eosin-stained cross-sections of the heart muscle of vehicle-treated mice showed the typical myocardial morphology of infarction with vacuolization of cardiomyocytes, edema, and infiltration of granulocytes and mononuclear cells. These histological signs are significantly less pronounced in heart tissue obtained from TAT-CrmA-treated mice.

Thus, TAT-CrmA protects myocardial tissue from apoptotic cell death during acute ischemic infarction even when administered simultaneously with the initiation of reperfusion. Apoptotic cardiomyocytes were detected by TUNEL staining, whereas vehicle-treated mice developed greater infarct sizes and more cardiomyocyte apoptosis in the infarct border zone after ischemia-reperfusion injury compared with TAT-CrmA-treated littermates, indicating that crmA limits myocardial tissue damage in vivo.

TABLE 1

Analysis of myocardial ischemia-reperfusion studies

|  | Sham operation | Tat-crmA administration before ischemia | | | Tat-crmA administration after ischemia | | |
| --- | --- | --- | --- | --- | --- | --- | --- |
|  |  | vehicle | TAT-crma | p-value | vehicle | TAT-crma | p-value |
| Number of animals tested | 3 | 5 | 5 |  | 13 | 13 |  |
| Body weight, g | 23.2 (±0.8) | 22.4 (±0.5) | 22.7 (±0.3) | 0.35 | 24.0 (±1.1) | 24.0 (±1.1) | 0.47 |
| Histology |  |  |  |  |  |  |  |
| Area at risk (AAR), mm$^2$ | 0 | 32.8 (±9.1) | 30.5 (±4.2) | 0.34 | 36.9 (±2.4) | 35.4 (±2.8) | 0.33 |
| Infarction size, mm$^2$ | 0 | 11.6 (±2.8) | 7.0 (±2.0) | 0.019 | 19.0 (±1.4) | 11.5 (±1.2) | <0.001 |
| Echocardiography |  |  |  |  |  |  |  |
| Heart rate, bpm | 445 (±12) | 414 (±46) | 440 (±22) | 0.32 | 434 (±8) | 417 (±11) | 0.12 |
| Ejection fraction, % | 71.0 (±3.7) | 22.6 (±1.7) | 50.7 (±4.9) | <0.001 | 23.2 (±4.9) | 39.3 (±4.2) | 0.002 |
| LVESV, µl | 15.3 (±1.1) | 48.9 (±4.5) | 28.0 (±2.9) | 0.004 | 53.3 (±3.2) | 39.6 (±2.8) | 0.003 |
| LVESV, µl | 54.7 (±3.1) | 62.9 (±5.1) | 58.0 (±4.7) | 0.22 | 70.5 (±2.4) | 64.2 (±2.8) | 0.06 |

The invention claimed is:

1. A fusion protein, comprising
   (a) a protein transduction domain capable of introducing the fusion protein into a mammalian cell, wherein said protein transduction domain comprises the amino acid sequence of SEQ ID NO:3; and
   (b) an anti-apoptotic protein comprising the amino acid sequence of SEQ ID NO:1.

2. The fusion protein of claim 1, wherein the fusion protein further comprises a linker between the protein transduction domain and the anti-apoptotic protein.

3. A pharmaceutical composition comprising the fusion protein of claim 1 and a physiologically acceptable carrier.

4. The pharmaceutical composition of claim 3, wherein said composition is formulated for injection.

5. A kit comprising i) the fusion protein of claim 1 and ii) one or more buffers, stabilizers or carriers.

6. An isolated polynucleotide encoding the fusion protein of claim 1.

7. An expression vector comprising the polynucleotide of claim 6.

8. An isolated host cell comprising the polynucleotide of claim 6.

9. A kit comprising i) the polynucleotide of claim 6, the expression vector of claim 7 or the host cell of claim 8, and ii) instructions for expressing and recovering the fusion protein of claim 1 from the polynucleotide, the expression vector or the host cell.

10. A method for preparing a fusion protein, comprising culturing of a host cell of claim 8 under conditions which allow for the expression of the fusion protein.

* * * * *

SEQUENCE LISTING

<160> NUMBER OF SEQ ID NOS: 7

<210> SEQ ID NO 1
<211> LENGTH: 344
<212> TYPE: PRT
<213> ORGANISM: Cowpox virus

<400> SEQUENCE: 1

Met Asp Ile Phe Arg Glu Ile Ala Ser Ser Met Lys Gly Glu Asn Val
1               5                   10                  15

Phe Ile Ser Pro Ala Ser Ile Ser Ser Val Leu Thr Ile Leu Tyr Tyr
                20                  25                  30

Gly Ala Asn Gly Ser Thr Ala Glu Gln Leu Ser Lys Tyr Val Glu Lys
            35                  40                  45

Glu Ala Asp Lys Asn Lys Val Ser Ala Gln Cys Ile Ser Phe Lys Ser
        50                  55                  60

Met Asn Lys Val Tyr Gly Arg Tyr Ser Ala Val Phe Lys Asp Ser Phe
65                  70                  75                  80

Leu Gly Lys Ile Gly Asp Lys Phe Gln Thr Val Asp Phe Thr Asp Cys
                85                  90                  95

Arg Thr Ile Asp Ala Ile Asn Lys Cys Val Asp Ile Phe Thr Gly Gly
            100                 105                 110

Lys Ile Asn Pro Leu Leu Asp Glu Pro Leu Ser Pro Asp Thr Cys Leu
        115                 120                 125

Leu Ala Ile Ser Ala Val Tyr Phe Lys Ala Lys Trp Leu Met Pro Phe
    130                 135                 140

```
Glu Lys Glu Phe Thr Ser Asp Tyr Pro Phe Tyr Val Ser Pro Thr Glu
145                 150                 155                 160

Met Val Asp Val Ser Met Met Ser Met Tyr Gly Glu Pro Phe Asn His
                165                 170                 175

Ala Ser Val Lys Glu Ser Phe Gly Asn Phe Ser Ile Ile Glu Leu Pro
            180                 185                 190

Tyr Val Gly Asp Thr Ser Met Met Val Ile Leu Pro Asp Lys Ile Asp
        195                 200                 205

Gly Leu Glu Ser Ile Glu Gln Asn Leu Thr Asp Thr Asn Phe Lys Lys
    210                 215                 220

Trp Cys Asn Ser Leu Glu Ala Thr Phe Ile Asp Val His Ile Pro Lys
225                 230                 235                 240

Phe Lys Val Thr Gly Ser Tyr Asn Leu Val Asp Thr Leu Val Lys Leu
                245                 250                 255

Gly Leu Thr Asp Val Phe Tyr Ser Thr Gly Asp Tyr Ser Asn Met Cys
            260                 265                 270

Asn Ser Asp Val Ser Val Asp Ala Met Ile His Lys Thr Tyr Ile Asp
        275                 280                 285

Val Asn Glu Glu Tyr Thr Glu Ala Ala Ala Thr Ser Val Leu Val
    290                 295                 300

Ala Asp Cys Ala Ser Thr Val Thr Asn Glu Phe Cys Ala Asp His Pro
305                 310                 315                 320

Phe Ile Tyr Val Ile Arg His Val Asp Gly Lys Ile Leu Phe Val Gly
                325                 330                 335

Arg Tyr Cys Ser Pro Thr Thr Asn
            340

<210> SEQ ID NO 2
<211> LENGTH: 341
<212> TYPE: PRT
<213> ORGANISM: Cowpox virus

<400> SEQUENCE: 2

Met Asp Ile Phe Arg Glu Ile Ala Ser Ser Met Lys Gly Glu Asn Val
1               5                   10                  15

Phe Ile Ser Pro Pro Ser Ile Ser Ser Val Leu Thr Ile Leu Tyr Tyr
                20                  25                  30

Gly Ala Asn Gly Ser Thr Ala Glu Gln Leu Ser Lys Tyr Val Glu Lys
            35                  40                  45

Glu Ala Asp Lys Asn Lys Asp Asp Ile Ser Phe Lys Ser Met Asn Lys
        50                  55                  60

Val Tyr Gly Arg Tyr Ser Ala Val Phe Lys Asp Ser Phe Leu Arg Lys
65                  70                  75                  80

Ile Gly Asp Asn Phe Gln Thr Val Asp Phe Thr Asp Cys Arg Thr Val
                85                  90                  95

Asp Ala Ile Asn Lys Cys Val Asp Ile Phe Thr Glu Gly Lys Ile Asn
            100                 105                 110

Pro Leu Leu Asp Glu Pro Leu Ser Pro Asp Thr Cys Leu Leu Ala Ile
        115                 120                 125

Ser Ala Val Tyr Phe Lys Ala Lys Trp Leu Met Pro Phe Glu Lys Glu
    130                 135                 140

Phe Thr Ser Asp Tyr Pro Phe Tyr Val Ser Pro Thr Glu Met Val Asp
145                 150                 155                 160

Val Ser Met Met Ser Met Tyr Gly Glu Ala Phe Asn His Ala Ser Val
```

```
                165                 170                 175
Lys Glu Ser Phe Gly Asn Phe Ser Ile Ile Glu Leu Pro Tyr Val Gly
            180                 185                 190

Asp Thr Ser Met Val Val Ile Leu Pro Asp Asn Ile Asp Gly Leu Glu
            195                 200                 205

Ser Ile Glu Gln Asn Leu Thr Asp Thr Asn Phe Lys Lys Trp Cys Asp
            210                 215                 220

Ser Met Asp Ala Met Phe Ile Asp Val His Ile Pro Lys Phe Lys Val
225                 230                 235                 240

Thr Gly Ser Tyr Asn Leu Val Asp Ala Leu Val Lys Leu Gly Leu Thr
            245                 250                 255

Glu Val Phe Gly Ser Thr Gly Asp Tyr Ser Asn Met Cys Asn Ser Asp
            260                 265                 270

Val Ser Val Asp Ala Met Ile His Lys Thr Tyr Ile Asp Val Asn Glu
            275                 280                 285

Glu Tyr Thr Glu Ala Ala Ala Thr Cys Ala Leu Val Ala Asp Cys
            290                 295                 300

Ala Ser Thr Val Thr Asn Glu Phe Cys Ala Asp His Pro Phe Ile Tyr
305                 310                 315                 320

Val Ile Arg His Val Asp Gly Lys Ile Leu Phe Val Gly Arg Tyr Cys
            325                 330                 335

Ser Pro Thr Thr Asn
            340

<210> SEQ ID NO 3
<211> LENGTH: 11
<212> TYPE: PRT
<213> ORGANISM: HI virus type 1

<400> SEQUENCE: 3

Tyr Gly Arg Lys Lys Arg Arg Gln Arg Arg
1               5                   10

<210> SEQ ID NO 4
<211> LENGTH: 401
<212> TYPE: PRT
<213> ORGANISM: Artificial Sequence
<220> FEATURE:
<223> OTHER INFORMATION: A Synthetic Fusion protein PTD-CrmA
<220> FEATURE:
<221> NAME/KEY: misc_feature
<222> LOCATION: (267)..(267)
<223> OTHER INFORMATION: Xaa can be any naturally occurring amino acid

<400> SEQUENCE: 4

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Leu Gly Tyr Gly Arg Lys Lys Arg Arg Gln Arg
            35                  40                  45

Arg Arg Gly Gly Ser Thr Met Ala Gly Thr Asp Ile Phe Arg Glu Ile
        50                  55                  60

Ala Ser Ser Met Lys Gly Glu Asn Val Phe Ile Ser Pro Ala Ser Ile
65                  70                  75                  80

Ser Ser Val Leu Thr Ile Leu Tyr Tyr Gly Ala Asn Gly Ser Thr Ala
                85                  90                  95

Glu Gln Leu Ser Lys Tyr Val Glu Lys Glu Ala Asp Lys Asn Lys Val
```

-continued

```
            100                 105                 110
Ser Ala Gln Cys Ile Ser Phe Lys Ser Met Asn Lys Val Tyr Gly Arg
        115                 120                 125
Tyr Ser Ala Val Phe Lys Asp Ser Phe Leu Gly Lys Ile Gly Asp Lys
    130                 135                 140

Phe Gln Thr Val Asp Phe Thr Asp Cys Arg Thr Ile Asp Ala Ile Asn
145                 150                 155                 160
Lys Cys Val Asp Ile Phe Thr Gly Gly Lys Ile Asn Pro Leu Leu Asp
                165                 170                 175
Glu Pro Leu Ser Pro Asp Thr Cys Leu Leu Ala Ile Ser Ala Val Tyr
            180                 185                 190
Phe Lys Ala Lys Trp Leu Met Pro Phe Glu Lys Glu Phe Thr Ser Asp
        195                 200                 205
Tyr Pro Phe Tyr Val Ser Pro Thr Glu Met Val Asp Val Ser Met Met
    210                 215                 220

Ser Met Tyr Gly Glu Pro Phe Asn His Ala Ser Val Lys Glu Ser Phe
225                 230                 235                 240
Gly Asn Phe Ser Ile Ile Glu Leu Pro Tyr Val Gly Asp Thr Ser Met
                245                 250                 255
Met Val Ile Leu Pro Asp Lys Ile Asp Gly Xaa Glu Ser Ile Glu Gln
            260                 265                 270
Asn Leu Thr Asp Thr Asn Phe Lys Lys Trp Cys Asn Ser Leu Glu Ala
        275                 280                 285
Thr Phe Ile Asp Val His Ile Pro Lys Phe Lys Val Thr Gly Ser Tyr
    290                 295                 300

Asn Leu Val Asp Thr Leu Val Lys Leu Gly Leu Thr Asp Val Phe Tyr
305                 310                 315                 320
Ser Thr Gly Asp Tyr Ser Asn Met Cys Asn Ser Asp Val Ser Val Asp
                325                 330                 335
Ala Met Ile His Lys Thr Tyr Ile Asp Val Asn Glu Glu Tyr Thr Glu
            340                 345                 350
Ala Ala Ala Ala Thr Ser Val Leu Val Ala Asp Cys Ala Ser Thr Val
        355                 360                 365
Thr Asn Glu Phe Cys Ala Asp His Pro Phe Ile Tyr Val Ile Arg His
    370                 375                 380

Val Asp Gly Lys Ile Leu Phe Val Gly Arg Tyr Cys Ser Pro Thr Thr
385                 390                 395                 400
Asn

<210> SEQ ID NO 5
<211> LENGTH: 1206
<212> TYPE: DNA
<213> ORGANISM: Artificial Sequence
<220> FEATURE:
<223> OTHER INFORMATION: A Synthetic DNA Encoding fusion protein PTD-
      CrmA

<400> SEQUENCE: 5
atgcggggtt ctcatcatca tcatcatcat ggtatggcta gcatgactgg tggacagcaa      60
atgggtcggg atctgtacga cgatgacgat aaggatcgat ggggatccaa gcttggctac     120
ggccgcaaga aacgccgcca gcgccgccgc ggtggatcca ccatggccgg taccgatatc     180
ttcagggaaa tcgcatcttc tatgaaagga gagaatgtat tcatttctcc agcgtcaatc     240
tcgtcagtat tgacaatact gtattatgga gctaatggat ccactgctga acagctatca     300
```

-continued

```
aaatatgtag aaaaggaggc ggacaagaat aaggttagcg ctcagtgtat ctcattcaag    360
tccatgaata aagtatatgg gcgatattct gccgtgttta aagattcctt tttgggaaaa    420
attggcgata agtttcaaac tgttgacttc actgattgtc gcactataga tgcaatcaac    480
aagtgtgtag atatctttac tggtgggaaa atcaatccac tattggatga accattgtct    540
cctgatacct gtctcctagc aattagtgcc gtatacttta aagcaaaatg gttgatgcca    600
ttcgaaaagg aattcaccag tgattatcca ttttacgtat caccgacgga aatggtagac    660
gtaagtatga tgtctatgta cggcgagcca tttaatcacg catctgtaaa agaatcattc    720
ggtaactttt caatcataga actgccatat gttggagata ctagtatgat ggtcattctt    780
ccagacaaga ttgatggatt rgaatccata gaacaaaatc taacagatac aaatttcaag    840
aaatggtgta actctctgga agctacgttt atcgatgtac atattcccaa gtttaaggta    900
acaggctcgt ataatcttgt ggatacgcta gtaaagttgg gactgacaga tgtgttctat    960
tcaaccggcg attatagcaa tatgtgtaat tcagatgtga gtgtcgacgc tatgatacac   1020
aaaacgtata tagatgtcaa tgaagagtat acagaagcag ctgcagcaac ttctgtacta   1080
gtggcagact gtgcatcaac agttacaaat gagttctgtg cagatcatcc gttcatctat   1140
gtgattaggc atgttgatgg caaaattctt ttcgttggta ggtattgctc tccaacaact   1200
aattaa                                                              1206
```

<210> SEQ ID NO 6
<211> LENGTH: 32
<212> TYPE: DNA
<213> ORGANISM: Artificial Sequence
<220> FEATURE:
<223> OTHER INFORMATION: A Synthetic PCR primer

<400> SEQUENCE: 6

```
ccgggtaccg atatcttcag ggaaatcgca tc                                   32
```

<210> SEQ ID NO 7
<211> LENGTH: 37
<212> TYPE: DNA
<213> ORGANISM: Artificial Sequence
<220> FEATURE:
<223> OTHER INFORMATION: A Synthetic PCR primer

<400> SEQUENCE: 7

```
ccggaattct taattagttg ttggagagca atatcta                              37
```